US006534012B1

(12) United States Patent
Hazen et al.

(10) Patent No.: US 6,534,012 B1
(45) Date of Patent: Mar. 18, 2003

(54) APPARATUS AND METHOD FOR REPRODUCIBLY MODIFYING LOCALIZED ABSORPTION AND SCATTERING COEFFICIENTS AT A TISSUE MEASUREMENT SITE DURING OPTICAL SAMPLING

(75) Inventors: Kevin H. Hazen, Phoenix, AZ (US); George Acosta, Phoenix, AZ (US); N. Alan Abul-Haj, Mesa, AZ (US); Roxanne E. Abul-Haj, Mesa, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 224 days.

(21) Appl. No.: 09/631,440

(22) Filed: Aug. 2, 2000

(51) Int. Cl.⁷ ............................................... G01N 21/47
(52) U.S. Cl. ................... 422/82.05; 436/164; 436/165; 422/50; 422/55; 422/68.1; 422/82.09; 422/108
(58) Field of Search ................... 436/164, 165; 422/55, 68.1, 82.05, 50, 82.09, 108; 250/214.1, 341.8; 356/445; 600/316, 342, 445

(56) References Cited

U.S. PATENT DOCUMENTS

| | | | | |
|---|---|---|---|---|
| 4,213,462 A | | 7/1980 | Sato | 128/634 |
| 4,548,505 A | * | 10/1985 | Ono | 356/445 |
| 5,036,853 A | * | 8/1991 | Jeffcoat et al. | 600/342 |
| 6,097,975 A | * | 8/2000 | Petrovsky et al. | 600/316 |
| 6,240,306 B1 | * | 5/2001 | Rohrscheib et al. | 600/316 |
| 6,353,226 B1 | * | 4/2002 | Khalil et al. | 250/341.8 |
| 6,403,944 B1 | * | 6/2002 | MacKenzie et al. | 250/214.1 |

FOREIGN PATENT DOCUMENTS

| | | | | |
|---|---|---|---|---|
| WO | 99/59464 | 11/1999 | | 21/47 |
| WO | 00/65988 | 11/2000 | | |
| WO | 0/109589 | 2/2001 | | 21/49 |

* cited by examiner

*Primary Examiner*—Jill Warden
*Assistant Examiner*—Brian Sines
(74) *Attorney, Agent, or Firm*—Glenn Patent Group; Michael A. Glenn; Christopher Peil

(57) ABSTRACT

An apparatus for varying localized absorption and scattering coefficients at a tissue measurement site in a controlled and reproducible manner during optical sampling of a tissue volume by controlling the pressure applied to a tissue measurement site by a spectroscopic analyzer allows applied pressure to be maintained at a constant level, or the applied pressure may be varied in a controlled, reproducible manner as a function of time. A rest for receiving a body part holds the body part in a fixed position and at a fixed elevation. A mechanical system advances a fiber optic probe until it makes contact with the body part with a constant amount of pressure. The applied force is supplied by a counterweight on a single arm balance. A temperature control allows the temperature of the fiber optic probe to be equilibrated with the temperature in the immediate vicinity of the tissue measurement site. Alternate embodiments allow the fiber optic probe to be brought into direct contact with the tissue measurement site, and displaced a known distance into the tissue. The invention is also embodied as a method in which the absorption and scattering coefficients for successive spectral measurements are calculated to determine optimum depth of penetration for detection of a target analyte.

56 Claims, 5 Drawing Sheets

APPARATUS AND METHOD FOR REPRODUCIBLY MODIFYING LOCALIZED ABSORPTION AND SCATTERING COEFFICIENTS AT A TISSUE MEASUREMENT SITE DURING OPTICAL SAMPLING

BACKGROUND OF THE INVENTION

1. Field of the invention

The invention relates to minimally invasive and noninvasive clinical testing. More particularly, the invention relates to an apparatus and method for modifying localized absorption and scattering coefficients at a tissue measurement site during optical sampling.

2. Description of the Related Art

Conventional methods of clinical testing have required the use of invasive procedures, such as biopsy and phlebotomy, to sample blood and tissue. Subsequently, the samples were transported to a central location, such as a laboratory, for examination and analysis. There is an increasing trend, however, toward point of care testing and even in-home testing. One of the benefits of this trend is to minimize the turnaround time from when a sample is taken to being able to take action based on the test results. At the same time, sampling procedures are becoming less and less invasive. Since they minimize or eliminate the need to handle blood and tissue specimens, minimally invasive and noninvasive procedures drastically reduce biohazard risk, both to the subject and the practitioner. Additionally, the decreased use of expendable reagents minimizes cost of testing and the environmental and health risks posed by the use of chemical substances.

Analyzers are being developed for point of care and in home use that either sample in a minimally invasive fashion or are completely noninvasive, often by sampling tissue optically. During use, it is necessary for many of these analyzers to contact the surface of a tissue measurement site directly, in order to control test conditions such as:

- stability of the analyzer during measurement;
- minimization of spectral reflectance;
- avoidance of stray light; and
- reproducibly hitting the targeted sampling area.

Pressure on the sampled tissue (skin) site induced by contact with the analyzer can result in localized sampling variations. For example, pressure applied to the tissue measurement site forces water from the vicinity of the site, decreasing the water concentration. As water concentration changes, there is a corresponding change in the local absorption coefficient. In addition, decreasing water concentration increases the density of the scattering centers present in the sampled tissue volume, thereby altering the reduced scattering coefficient. It would be desirable to modify local absorption and reduced scattering coefficients in a controlled, reproducible manner, allowing differential measurements to optimize the signal-to-noise ratio of one or more target analytes.

It would also be advantageous to provide sampling devices that either maintain a constant pressure or displacement between the analyzer and the subject's skin or that reproducibly control changes in pressure or displacement over time.

SUMMARY OF THE INVENTION

The invention provides a subject interface module for modifying localized absorption and scattering coefficients by controlling the pressure applied to a tissue measurement site by an analyzer during optical sampling; the applied pressure may be maintained at a constant level, or it may be applied in a controlled, reproducible manner as a function of time, so that absorption and reduced scattering coefficients may be varied in a controlled, reproducible manner. The invention is also embodied as a method of modifying localized absorption and scattering coefficients in a controlled and reproducible manner by varying pressure or displacement during optical sampling.

The preferred embodiment of the invention includes a placement device for receiving a body part such as an arm, so that the body part is held in a fixed position and at a fixed elevation. The invention further includes an applied force mechanism for advancing the fiber optic probe of an analyzer until it makes contact with the body part, and maintaining the contact at a constant pressure. The applied force is supplied by a counterweight on a single arm balance. The invention further provides a temperature control, for equilibrating the temperature of the fiber optic probe with the surface temperature in the immediate vicinity of the tissue measurement site.

Alternate embodiments of the invention provide a means for bringing the fiber optic probe into contact with the surface of the tissue measurement site, and then displacing it by a known distance. In one embodiment, an LED and a detector define a starting location prior to displacement and the fiber optic probe is displaced a given distance after the LED is detected. In another embodiment, the displacement of the probe is dictated by the elimination of spectral reflectance. In a further embodiment, the probe is displaced into the tissue until analysis of the spectral information indicates that the preferred depths of the sample are being probed.

DETAILED DESCRIPTION

Figure 1:
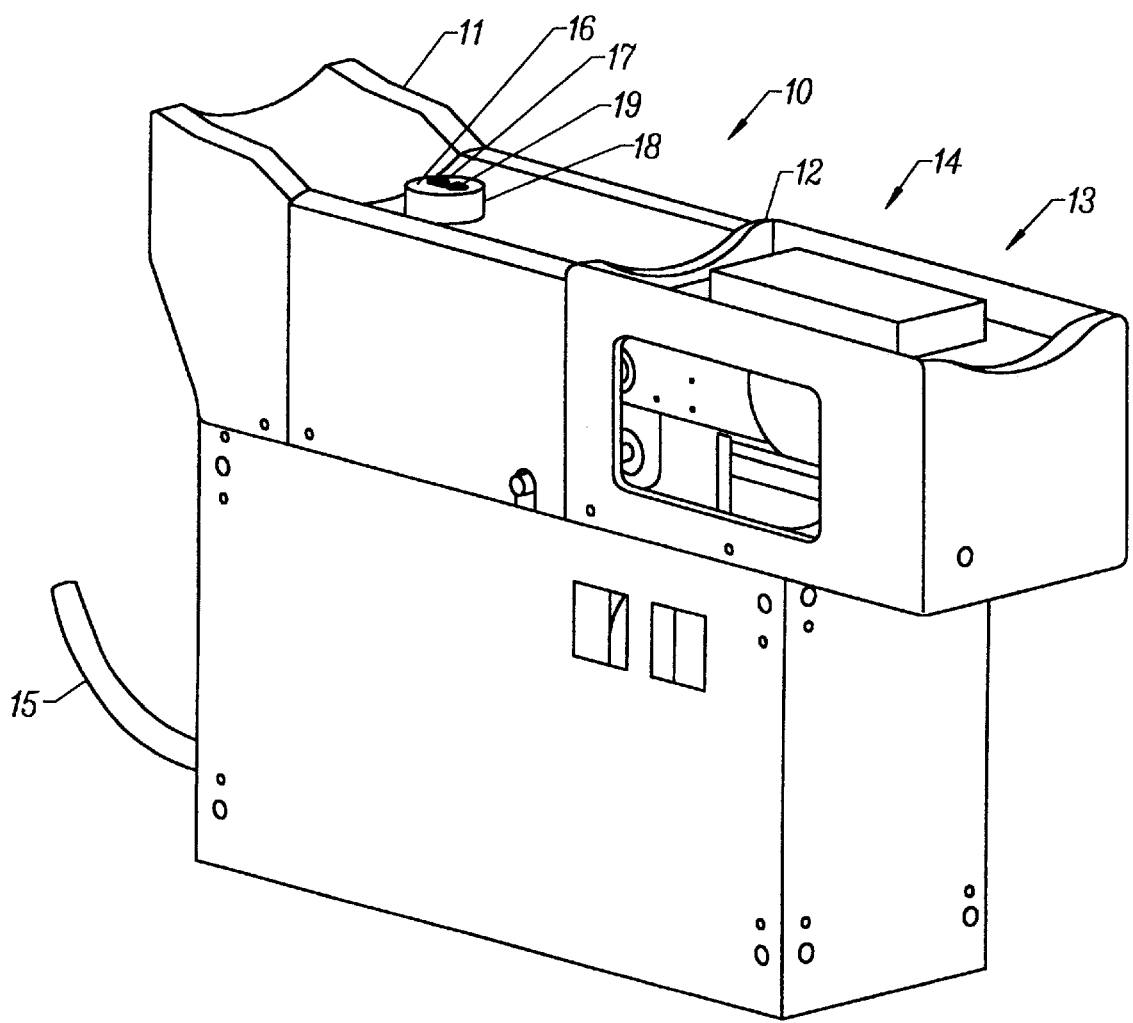
FIG. 1 provides a three-dimensional view of an arm support guide, according to the invention.

The application of pressure to a sampling area in a noninvasive measurement may affect the measurement site in a number of ways, including:

- localized changes in analyte concentration;
- localized changes in physical parameters, such as temperature; and
- changes in absorption and scattering coefficients.

For example, as pressure is applied to a region of the body, the localized water concentration changes due to the applied pressure forcing water out of the area. Subsequently, internal blood pressure is increased to maintain blood flow to the area. Both affects alter the localized water concentration with different time constants. As the water concentration changes, multiple additional localized parameters change. In the near-IR spectral region, the absorption coefficient, $\mu_a$, decreases as water concentration decreases. With less water, the density of the scattering centers increases, with a resulting increase in the reduced scattering coefficient, $\mu'_s$. Naturally, the $\mu_a/\mu'_s$ ratio also changes, since both coefficients have changed. In addition, the concentrations of all analytes carried in the blood or interstitial fluid change over a localized volume as they are expelled from the area along with the water. As a result of water movement, non-aqueous analytes will also experience localized concentration changes. For example, as water departs a given volume of tissue, the relative concentration of the remaining non-aqueous analytes increases.

During a non-invasive measurement, the penetration of photons into the tissue layers is dependent upon the pressure applied to the tissue. As previously indicated, pressure applied to a localized area changes the water concentration, resulting in a localized change in the scattering and absorption coefficients. As the scattering properties of the tissue change, indicated by changes in the scattering coefficient, the depth of penetration of photons changes. As a result, the sampled volume of the tissue changes. Since the tissue measurement site is not of a homogeneous nature, but is rather composed of layers, alterations in sampled volume can have a pronounced affect on the measurement. To a first approximation, the skin comprises a series of layers, starting with the stratum corneum at the surface, followed in turn by the epidermis, the dermis, and a subcutaneous fat layer, with internal structures, such as organs and bone, finally found far beneath the skin. Each layer has a different mean concentration of each analyte and interferent. Accordingly, as the mean depth of penetration of the probing photons changes, so does the mean concentration of analytes and interferents. Thus, for a given sample, application of differing pressures results in spectra that sample different tissue volumes, each containing different concentrations of target analyte and interferents. Pressure on the measurement site must either be kept constant or varied in a controlled, reproducible manner, so that the impact of variation of pressure on the sampling site may be well characterized, allowing appropriate development of algorithms that compensate for or take advantage of the different sampled volumes.

In noninvasive analysis, pressure effects are most evident in the near-IR and mid-IR regions, which sample the surface layers. Applied pressure changes localized concentrations over a limited radial distance from the point of contact and to limited depths. Thus, photons that predominantly sample the affected area are most affected by pressure. The depth of penetration of near-IR and mid-IR photons is limited by the strong absorbance of water. Scattering centers in the tissue also limit the depth of penetration of light, from the ultraviolet through the visible and into the near-IR range. Since these spectral regions sample depths in tissue where pressure has the most effect, they will be the most sensitive to pressure. It should be noted that the affects will be observed the most in diffuse reflection based analyzers but will also affect transflectance based measurements and will have some affect on transmission based measurements.

Advantageously, the foregoing effects on localized absorption and scattering coefficients are applied in a method that utilizes differential spectral measurements during which the applied force is varied by a known amount to modify localized absorbance and scattering coefficients in a controlled manner. The resulting values for the $\mu_a/\mu'_s$ ratio are then utilized in a differential measurement to enhance the signal-to-noise ratio of a target analyte signal. For example, the observed absorbances of particular components such as water, protein, fat or urea reach a known level or a given ratio versus another component. These ratios may be calibrated at known pressures or displacement levels for individuals or groups of subjects using any of a large number of combined wavelengths with known chemometric techniques.

In summary, the invented method includes the steps of:
providing a tissue measurement site;
a providing a spectroscopic analyzer having a subject interface adapted to make direct contact with the tissue measurement site during measurement;
making an initial spectral measurement, in which the applied pressure or displacement by the analyzer is known and maintained during the measurement;
calculating the absorbance and scattering coefficients;
making subsequent measurements in which the applied pressure or displacement is varied by a known amount, and calculating absorbance and scattering coefficients for each measurement; and
determining an optimal sampling depth for detecting a target analyte based on the ratio of the measured absorption coefficients and scattering coefficients.

The invention is further embodied as an apparatus for modifying localized absorption and scattering coefficients by varying pressure or displacement on a tissue measurement site in a controlled and reproducible manner. According to a preferred embodiment, the invention provides a subject interface module for adjustably maintaining pressure applied to a tissue measurement site from a fiber optic probe at a constant level during optical sampling. While the preferred embodiment of the invention utilizes a bifurcated fiber optic bundle that couples light from the light source of an analyzer to the tissue measurement site and from the tissue measurement site to the detector element of the analyzer, other means of coupling light from a light source to a target site would be suitable in the invention as well. The constant force subject interface module consists of two major elements: a placement guide for securing the subject's body part upon which the tissue measurement site is located, and an adjustable applied force mechanism.

While the invention has been described herein with reference to human subjects, this description is exemplary only and not intended to limit the scope of the invention. Additionally, the placement guide has been described with respect to the human arm. The principles of the invention will suggest other guides to those skilled in the art that are applicable to other limbs and body parts, both human and non-human, that are consistent with the spirit and scope of the invention. Referring now to FIG. 1, shown is an arm placement guide 10. The arm placement guide is equipped with an elbow guide 11 and a wrist guide 12. While the invented guide also aids in supporting and immobilizing the arm, its primary function is to enable reproducible placement of the tissue measurement site on the analyzer, critical in producing accurate, consistent noninvasive measurements. During use, a subject in a sitting position places the arm to be sampled in the arm placement guide, so that the elbow is received by the elbow guide 11 and the wrist and hand are positioned on the ergonomically shaped wrist guide 12 and hand guide 13. In the resulting position, the sample arm is at the subject's side with the elbow flexed to 90°. In the current embodiment, the arm placement device exhibits "handedness;" that is, arm placement devices are separately adapted to receive right or left arms, respectively.

Figure 2:
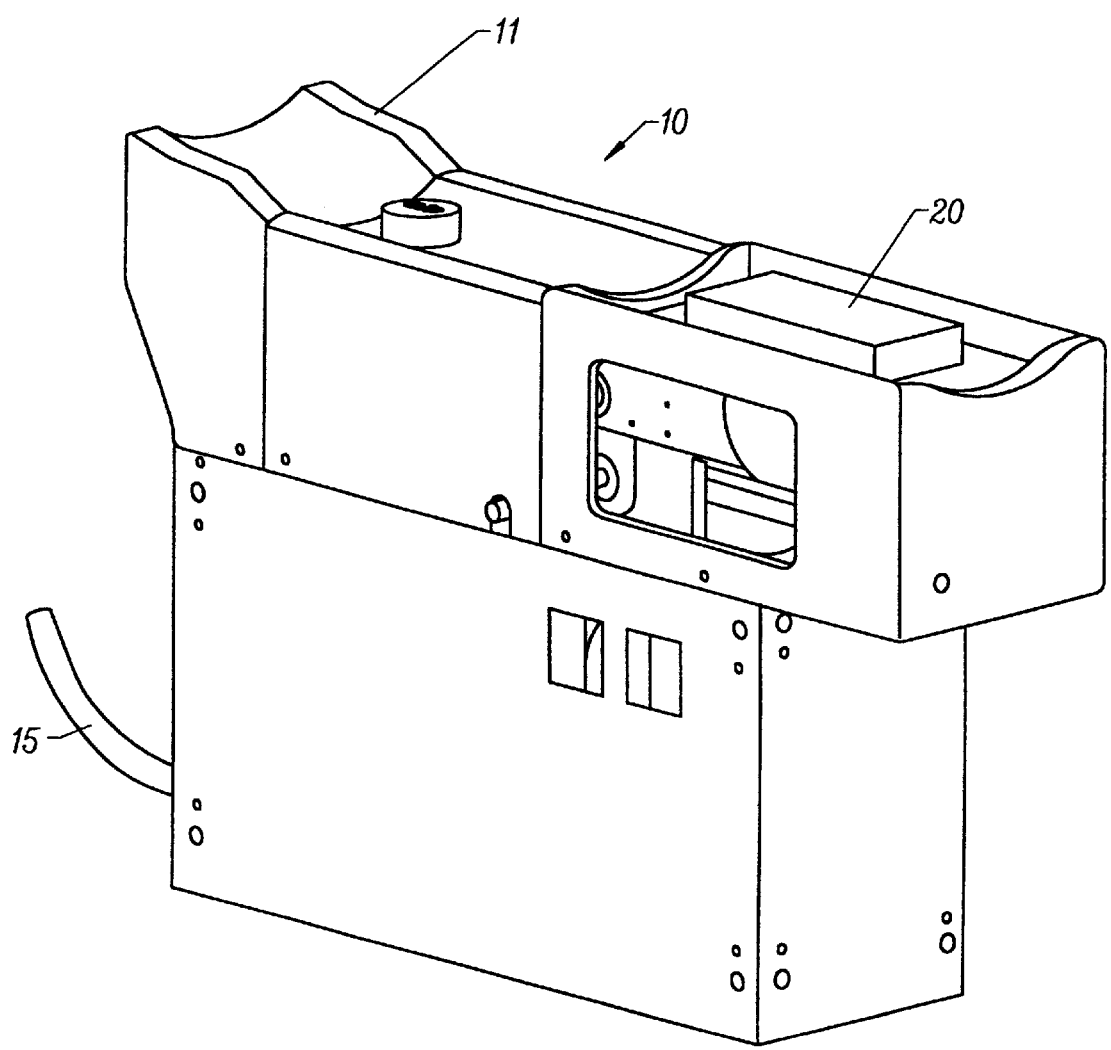
FIG. 2 provides a three-dimensional view of the arm support guide of FIG. 1 with a wrist guide and hand guide removed, according to the invention.

It is preferred that the subject be in a sitting position during actual sampling, to minimize the effects of size difference between subjects. During tests of the invented device, sampling with the subject in a sitting position resulted in only a 2" difference in the height of the arm between an adult male and 10 year old boy, allowing the current embodiment of the invention to be built with a relatively small range of travel being required by the movable fiber optic probe. The wrist/hand guide unit 15 is detachably mounted on a mechanical slide 20 (FIG. 2) allowing the wrist support to be positioned directly under the subject's wrist regardless of arm length. For optimal reproducibility in placement of the arm on the analyzer, a custom elbow guide 11 and wrist/hand guide 14 are constructed by creating custom molds of a subject's elbow, wrist and hand. In the preferred embodiment, the molds are formed from a substance such as the 5-minute RTV (room temperature vulcanization) silicone putty supplied by Micro-Mark of Berkeley Heights N.J., which is FDA approved for skin contact. However, other products used for mold making having the appropriate toxicity profile would be equally suitable.

As previously indicated, a fiber optic probe employs a bifurcated fiber optic cable 15 to deliver light energy to the tissue measurement sight from an energy source (not shown). The same probe collects light energy reflected or transmitted from the tissue measurement site and delivers it to detectors (not shown). A subject interface includes a cylindrical housing 16 with the fiber optic probe tip 17 protruding from a terminal surface of the cylindrical housing. An aperture 18 in the arm placement guide provides the subject interface access to the tissue measurement site.

The subject's arm is positioned in the arm guide 10 such that the lowest point of the suspended forearm is suspended directly over the tip of the fiber optic probe 17. While the arm is being positioned, the fiber probe tip 17 is locked into a 'down' position using the beam movement brake 34 (FIG. 3) described in greater detail below.

Figure 3:
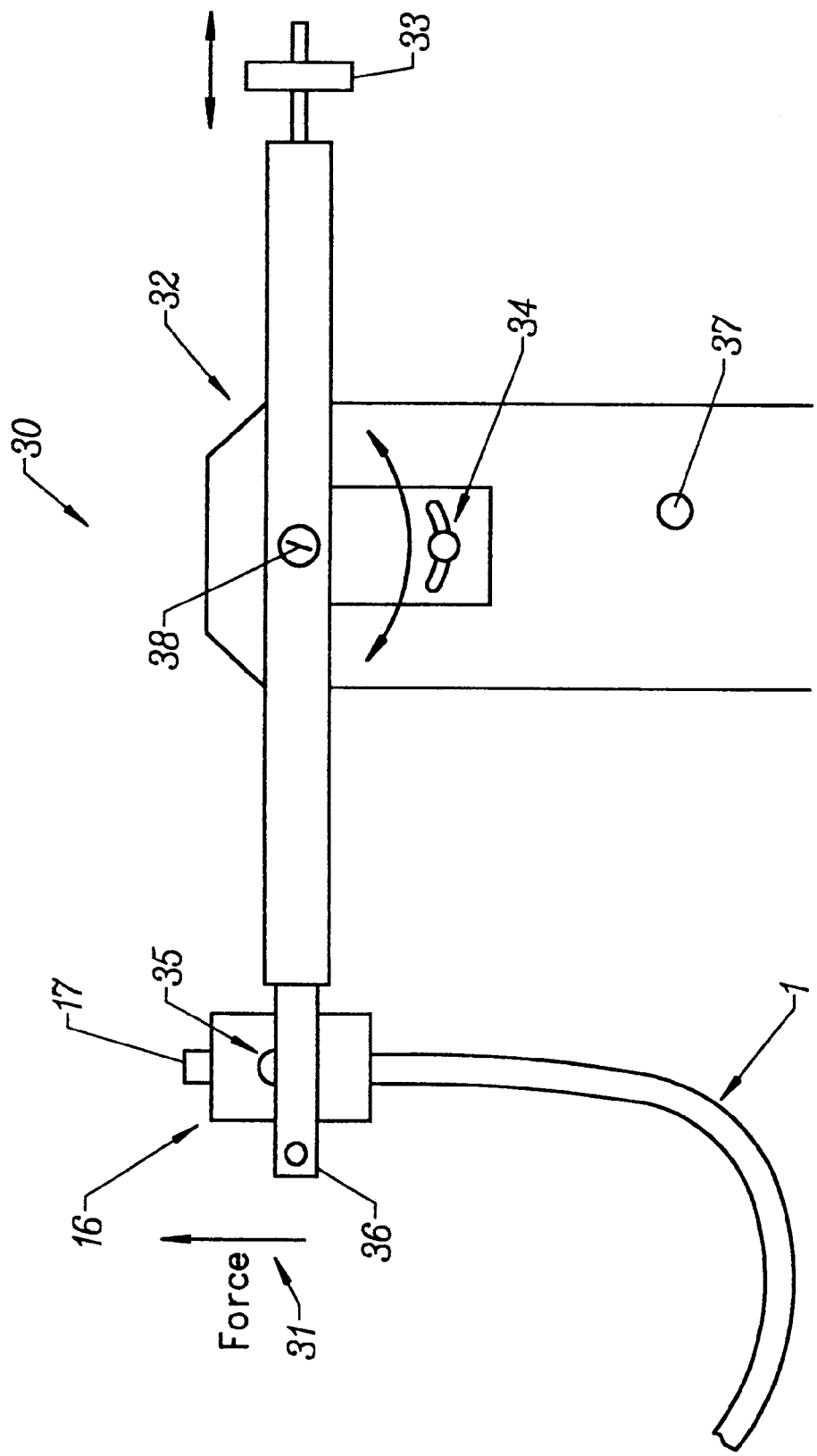
FIG. 3 shows a schematic view of an applied force mechanism for advancing a fiber optic probe, according to the invention.

Once the arm is positioned, an applied force mechanism 30 incorporating a conventional single arm balance is employed to move the fiber optic probe tip 17 upward until it contacts the arm with a constant upward force 31, shown in FIG. 3. In order to apply a very small, known amount of force to the arm with the fiber optic probe, the point of contact between the forearm and the probe should be limited to the tip of the probe. It is preferable that the fiber optic probe be rectangular, with the long side of the rectangle oriented lengthwise on the arm, so that the entire probe may contact the arm with a minimal application of pressure. Additionally, the head of the fiber optic probe needs to be as small as possible; again, in order to minimize the amount of pressure required for complete contact between the probe and the tissue measurement site. In the current embodiment, the applied force is provided by a counterweight 33 on a single arm balance. The balance comprises a hinged beam 32, mounted on an upright mount 37, that rotates about a point of rotation defined by the point of attachment to the upright mount. A bearing 38 allows free movement of the beam about the point of rotation. As the adjustable weight 33 is moved along the axis of the beam, the force 31 applied to the tissue measurement site by the fiber optic probe is changed. An alternative arrangement (not shown) for the adjustable weight incorporates a weight that slides along the arm of the balance, which is provided with gradations for different pressure levels. A screw with a small circular weight mounted on it may be used for fine adjustments to the applied force. In the present embodiment of the invention, the total applied pressure may be varied in a continuous fashion from 0 to 2 $kg/in^2$. Additional weights may be added to vary the applied force as required. Once the fiber optic probe is positioned, the probe may be locked into position with the beam movement brake/lock mechanism 34. The beam movement brake functions by means of a friction plate, which is compressed into the upright mount 37 to lock the beam at a desired position. In addition, the subject interface floats on a gimbal mount 35 to insure that the optical axis of the probe is normal to the subject's arm at the point of contact. The gimbal mount includes a gimbal locking mechanism 36 that locks the gimbal by means of a compression or pinch element. The fiber optic probe tip may be locked into position with the gimbal locking mechanism 36 to maintain the stability of the probe against the arm. In order to further assure the reproducibility of arm placement, it is necessary to protect the invented apparatus from structural deformation due to excessive pressure applied by the subject in the event that they lean on the analyzer. The entire structure of the current embodiment is designed, therefore, to withstand a force of 200 pounds exerted upon the arm support structure, without deforming.

In addition to pressure control, the apparatus is capable of controlling the temperature of the fiber optic probe so that it may equilibrate to the localized temperature in the vicinity of the tissue measurement site. In the current embodiment, the housing 16 is cylindrical and completely surrounds the fiber optic probe, with the probe tip 17 protruding from a terminal surface of the cylindrical housing 16. Within the housing is a metallic core that is maintained at a given temperature by means of a low voltage temperature device (not shown). In the current embodiment, the core is fabricated from aluminum, although other metals that are lightweight and conduct heat readily would also be suitable. The temperature device is equipped with a feedback control, allowing it to maintain a constant temperature. It should be noted that the temperature of the sampled area may be predicted from the near-IR spectra by using the shifts of the water bands, which absorb at 1450, 1950 and 2600 nm. As the temperature of the water increases, these bands shift to higher energy.

The localized temperature of the forearm may also be measured directly. A thermistor 19 encapsulated in a housing protrudes from the housing 16 into the forearm slightly at a distance of approximately 7 m from the edge of the fiber optic probe tip. In combination with temperature readings inside the housing, the localized forearm temperature at the tissue measurement site may be calculated.

One skilled in the art will recognize that the pressure may be applied by a variety of other means, including but not limited to: a lever arm, spring force, air pressure or counter weights. While the above system is calibrated with counter weights, one skilled in the art will recognize that the applied pressure may be measured by a variety of means, including but not limited to: balances, air pressure gauges, or by calculation.

An alternate version of the arm placement guide is reproducibly attached to the arm and has guide rods that couple to the spectrometer to aid in reproducibly coupling the sample to the analyzer.

While the preferred embodiment described above utilizes an applied force to generate an applied pressure between the analyzer and the tissue measurement site, in an alternate embodiment, the analyzer is brought into contact with the tissue measurement site and subsequently displaced a known distance against the skin at the tissue measurement site. In the current, alternate embodiment of the invention, the fiber optic probe is maintained in a fixed vertical position, as it protrudes from a platform upon which the subject's limb rests. The platform is raised and lowered, allowing the tip of the fiber optic probe to compress the skin at the tissue measurement site by varying amounts. Different versions of the current embodiment, each employing a different method for determining degree of displacement, are provided. First, an LED and detector define a starting location prior to displacement and the subject interface module may be displaced a given distance after the LED is detected. Second, the analyzer may be moved until spectral reflectance is removed, or, optionally, moved a fixed distance after elimination of spectrally reflected light. In the near-IR this would be-when the light intensity at 1950 nm, where water has a strong absorbance, approaches zero. Third, the analyzer may be displaced into the tissue until analysis of the spectral information indicates that the preferred depths of the sample are being probed, indicated by the detection of chemical bands that serve as markers for an individual subject or class of subjects; described in detail in the commonly assigned U.S patent application Ser. No. 09/359,191, An Intelligent System For Noninvasive Blood Analyte Prediction, S. Malin, T. Ruchti (Jul. 22, 1999). Each of these versions is described in greater detail below.

Figure 4:
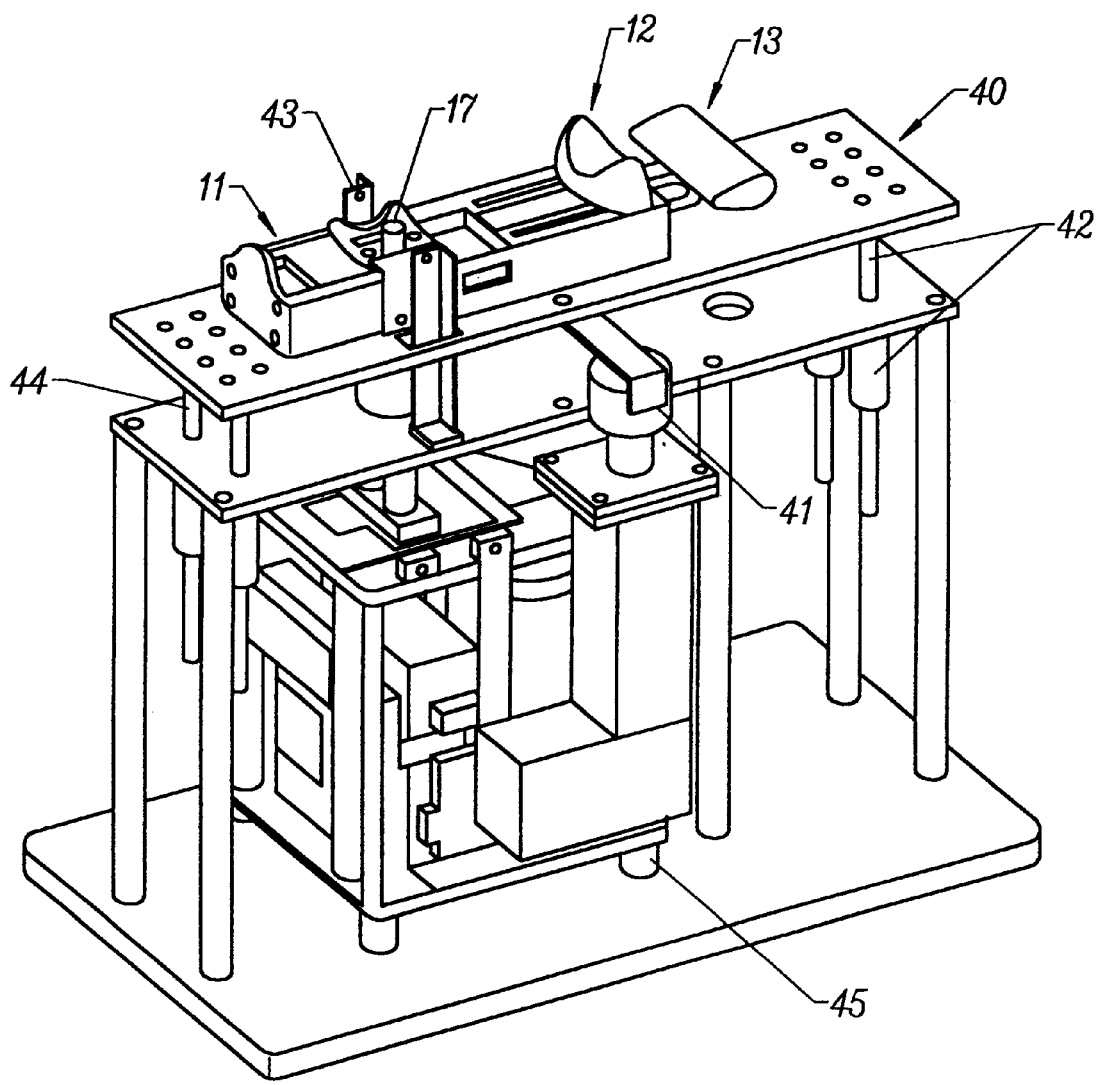
FIG. 4 provides a three-dimensional view of a constant displacement subject interface module, according to the invention.

Referring now to FIG. 4, the current embodiment of the invention provides ergonomically designed elbow 11, wrist 12 and hand 13 guides mounted on an arm support platform 40. Protruding through the arm support platform 40 is the fiber optic probe 17. The arm support platform 40 is moved vertically up and down by a linear actuator mechanism composed of an actuator arm 41 and vertical guides 42. The linear actuator mechanism is driven by a conventional electric motor 45, which is, in turn, controlled by a digital processor (not shown). An LED 43 situated at one side of the subject's arm aims directly above the fiber bundle 17 and is detected by a detector 44 situated at the opposite side of the subject's arm. During use, the subject rests their arm on the provided elbow 11, wrist 12, and hand guides 13. The linear actuator lowers the platform bearing the subject's arm toward the fiber optic probe by lowering the arm support platform 40. As the arm breaks the plane defined by the LED 43 and the corresponding detector 44, the LED signal is lost, and the system recognizes that the tissue measurement site is a known distance from the tip of the fiber optic probe 17, the zero position. The arm support plane may be further lowered in a controlled manner allowing known displacements of the fiber optic probe into the subject's forearm. Naturally, the elasticity of living tissue allows varying pressures to be applied to the surface of the tissue measurement site without actual penetration of the fiber bundle into the skin of the arm.

Figure 5:
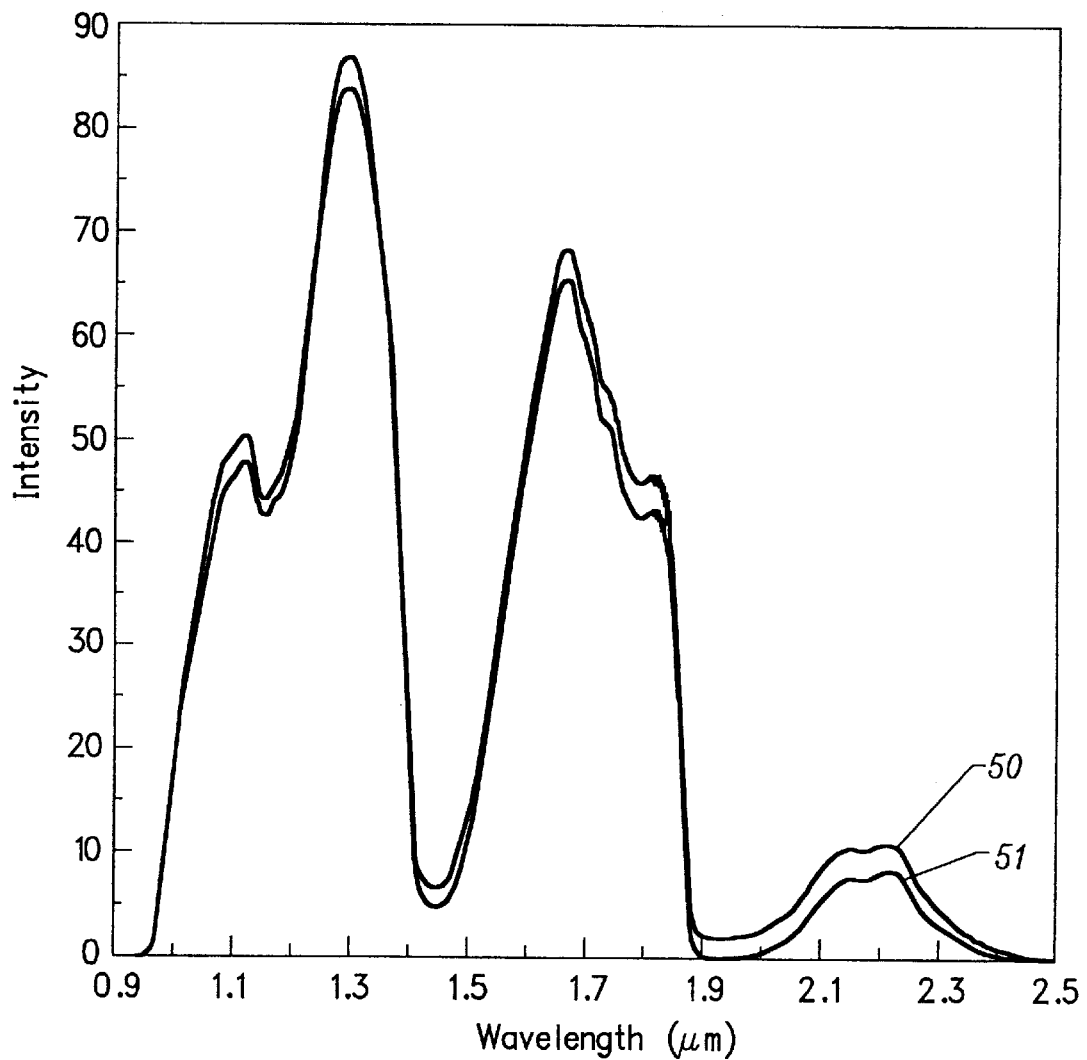
FIG. 5 provides two noninvasive diffuse reflectance spectra of a tissue measurement site on a human forearm, according to the invention.

A second version of the constant displacement subject interface module defines the zero position of the translating arm support plane by detecting spectrally reflected light collected by the fiber optic probe. The zero position constitutes the point at which no spectrally reflected light is detected. When the tissue measurement site is not in contact with the surface of the fiber optic probe, spectrally reflected light may be collected in the probe and detected. This spectrally reflected light is an interferent that hinders analysis. When the tissue measurement site first makes complete contact with the tip of the fiber optic probe, the spectrally reflected light approaches zero intensity. In a diffuse reflectance based measurement of the skin in the near-IR region, water has several strong absorbance bands located at 1450, 1950 and 2600 nm. Two noninvasive diffuse reflectance spectra of a tissue measurement site on a human forearm are shown in FIG. 5. The top curve 50 shows that light is being detected at 1950 and 2500 nm, in a region where water has sufficiently high absorbance levels that a zero signal should be observed. The detection of light indicates that spectrally reflected light is being collected and that the fiber optic probe and the tissue measurement site are not in contact. The lower curve 51 shows zero intensity (noise limited intensity) at 1950 and 2500 nm, indicating that the fiber optic probe tip and the tissue measurement site are in direct contact. The zero point is defined as the point when intensity at 1950 nm first reaches zero. Known displacements beyond this point are determined using the distance of travel of the computerized arm support platform.

A third version of the constant displacement subject interface module establishes the displacement of the fiber optic probe into the forearm using spectral information. As previously discussed, the scattering and absorption coefficients of the sample change with different degrees of applied pressure. Therefore, the sampled volume and resulting spectra are a function of the displacement of the fiber versus the zero position. Thus, the spectra may be used to create a feedback to the linear drive system as to the desired displacement of the subject interface module.

Other systems for raising and lowering the arm support platform are possible, including: a hand crank, a lever arm, a scissors jack and drive, a hinge point in conjunction with a linear drive and a worm drive. Other systems consistent with the spirit and scope of the invention will be apparent to those skilled in the art.

There are many situations in which it is beneficial to control the amount of pressure exerted by an analyzer on the sample being analyzed. In the biomedical field, analyzers are under development for a variety of important analytes; for example, glucose, for monitoring diabetics, urea, for use with dialysis patients, and oxygen. As previously mentioned, point of care testing using minimally invasive and non-invasive methods is rapidly supplanting more conventional methods of sampling and laboratory analysis in the field of clinical testing. The invention finds application in any minimally invasive and non-invasive measurements of this type, in which an analyzer must make contact with a tissue measurement site.

While the foregoing description has presented the invention in the context of medical applications with human subjects, the invention finds broad application in a number of technical fields where solid samples are analyzed that are not homogeneous at or near the surface and are elastic, or where spectral reflectance must be eliminated by directly contacting a sample with an analyzer. For example, the invention may be readily adapted for veterinary or research use with non-human subjects. Additionally, optical sampling of agricultural products is exceedingly common. For example, analyses of fruits, vegetable and grains are affected by the degree of pressure applied to the sample by the analyzer. The invention also provides an apparatus for the removal of spectrally reflected light off of a sample in diffuse reflectance mode, which is critical to quantitative analysis of small analyte signals. Within the pharmaceutical and chemical arts, intimate contact of the analyzer with tablets, capsules, pellets, chips and other such items is beneficial in diffuse reflectance based measurements.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

What is claimed is:

1. An apparatus for varying localized absorption and scattering coefficients at a tissue measurement site in a controlled and reproducible manner during optical sampling comprising:

a subject interface for variably contacting with a tissue measurement site;

means for measuring specular reflectance or spectral data of tissue at said tissue measurement site;

means for varying and maintaining contact with said tissue measurement site by said subject interface in a controlled and reproducible manner according to any of said measured specular reflectance and said measured spectral data; and means for reproducibly positioning said tissue measurement site relative to said subject interface.

2. The apparatus of claim 1, wherein said subject interface comprises:

a fiber optic probe surrounded by a housing, wherein said probe delivers light energy to said tissue measurement site and collects light energy transmitted or reflected from said tissue measurement site.

3. The apparatus of claim 2, wherein a tip of said fiber optic probe contacts said tissue measurement site, where said tissue measurement site is located on a limb of said subject.

4. The apparatus of claim 3, wherein said fiber optic probe is rectangular and wherein said probe tip contacts said limb in a lengthwise manner so that contact of said probe tip with said tissue measurement site is maximized, with a minimum of applied pressure to said tissue measurement site by said probe tip being required.

5. The apparatus of claim 2, wherein said housing comprises a cylinder surrounding said fiber optic probe and wherein said probe tip protrudes from a terminal surface of said housing.

6. The apparatus of claim 5, wherein said housing is fabricated from a lightweight, heat conductive material.

7. The apparatus of claim 6, wherein said housing further comprises means for heating said fiber optic probe so that probe temperature is equilibrated with surface temperature at said tissue measurement site.

8. The apparatus of claim 7, said subject interface further comprising means for detecting surface temperature at said tissue measurement site.

9. The apparatus of claim 2, wherein said means for varying and maintaining contact with said tissue measurement site by said subject interface in a controlled and reproducible manner comprises:

a single arm balance with a counter weight, said single arm balance comprising a hinged beam attached to an upright mount at a point of attachment, wherein a bearing element allows said hinged beam to rotate freely about a point of rotation defined by said point of attachment, and wherein said beam has a first end and a second end; and a gimbal mount attached to said second end for receiving said subject interface;

wherein adjusting said counter weight varies the amount of pressure applied to said tissue measurement site by said fiber optic probe.

10. The apparatus of claim 9, wherein said subject interface floats on said gimbal mount so that the optical axis of said fiber optic probe is normal to a limb of said subject whereon the tissue measurement site is located when the fiber optic probe is pressing against said tissue measurement site.

11. The apparatus of claim 10, wherein said gimbal mount is equipped with a gimbal locking mechanism, said gimbal locking mechanism comprising any of a compression and a pinch element and wherein said gimbal locking mechanism is operative to maintain stability of said fiber optic probe tip against said tissue measurement site.

12. The apparatus of claim 9, wherein said counter weight comprises an adjustable weight attached at said first end of said hinged beam.

13. The apparatus of claim 9, wherein said counter weight comprises a larger weight that slides along said beam, where said beam has gradations for different pressure levels, and wherein a screw with a smaller weight attached at said first end allows fine adjustments to applied pressure.

14. The apparatus of claim 9, further comprising a beam movement brake mechanism, said beam movement brake mechanism comprising a friction plate, said friction plate being operative to lock said beam into a desired position by being compressed against said upright mount.

15. The apparatus of claim 1, wherein said means for reproducibly positioning said tissue measurement site relative to said subject interface comprises a limb guide for receiving a limb of said subject, whereon said tissue measurement site is located.

16. The apparatus of claim 15, wherein said limb guide comprises an arm guide, said arm guide comprising:

a platform mounted on a support structure;

an elbow guide; a wrist guide and a hand guide, all detachably mounted on said platform; and an aperture defined by said platform.

17. The apparatus of claim 16, wherein said arm guide receives said subject's arm, so that the subject's elbow is resting in the elbow guide, the subject's wrist is resting on the wrist guide and the subject's hand is resting on the hand guide such that a tissue measurement site on a lower surface of said arm is aligned with said aperture.

18. The apparatus of claim 17, wherein said subject interface, mounted on said means for varying and maintaining contact with said tissue measurement site protrudes upward through said aperture to contact said tissue measurement site.

19. The apparatus of claim 16, wherein said wrist guide and said hand guide are formed as a single unit, and wherein said unit is slideably mounted on said platform, so that said unit is positionable according to the length of said subject's forearm.

20. The apparatus of claim 19, wherein said elbow guide and said assembly are ergonomically molded.

21. The apparatus of claim 20, wherein said elbow guide and said assembly are custom molded according to subject.

22. The apparatus of claim 17, wherein said subject's arm is positioned such that the arm is at the subject's side and flexed to an angle of ninety degrees.

23. The apparatus of claim 16, wherein said arm guide is adapted to receive one of a right arm and a left arm.

24. The apparatus of claim 2, wherein said means for reproducibly positioning said tissue measurement site relative to said subject interface comprises a platform, said platform being supported by and attached to said means for varying and maintaining contact with said tissue measurement site by said subject interface in a controlled and reproducible manner, said means for varying and making contact comprising:

a system for raising and lowering said platform so that said fiber optic probe may be brought into contact with said tissue measurement site and then displaced into skin at the tissue measurement site by a known amount, where said subject interface is fixedly mounted;

wherein said tissue measurement site is located on an arm of said subject.

25. The apparatus of claim 24, wherein said platform has detachably mounted thereon;
   an elbow guide, a wrist guide and a hand guide for reproducibly positioning said arm, said wrist guide and said hand guide being slideable to accommodate arms of varying length; and
   wherein said platform has an aperture through which said fiber optic probe protrudes in order to make contact with the tissue measurement site.

26. The apparatus of claim 25, wherein said elbow guide, said wrist guide and said hand guide are ergonomically molded.

27. The apparatus of claim 25, wherein said guides are custom molded according to subject.

28. The apparatus of claim 25, wherein said subject's arm is positioned such that the arm is at the subject's side and flexed to an angle of ninety degrees.

29. The apparatus of claim 25, wherein said system for raising and lowering said platform comprises a linear slide mechanism, said linear slide mechanism comprising an actuator arm and a plurality of vertical guides.

30. The apparatus of claim 29, said system for raising and lowering said platform further comprising an electric motor for driving said linear slide mechanism.

31. The apparatus of claim 30, wherein said motor is computer-controlled.

32. The apparatus of claim 31, wherein a zero point constitutes the elevation at which full contact between said arm and said fiber optic probe first occurs.

33. The apparatus of claim 32, said system further comprising:
   an LED situated at one side of said arm;
   a detector situated at the opposite side of said arm;
   wherein a signal from said LED is aimed directly above said fiber optic probe, and detected by said detector.

34. The apparatus of claim 33, wherein said arm is lowered until said zero point is reached, said zero point constituting the elevation at which said LED signal is undetectable.

35. The apparatus of claim 32, wherein said zero point is determinable by analyzing successive spectral measurements for spectrally reflected light, and wherein an absence of spectrally reflected light indicates said zero point.

36. The apparatus of claim 32, wherein said subject's arm is positioned at said zero point and subsequently lowered onto said fiber optic probe so that said probe is displaced into the skin of said tissue measurement site by a preferred amount, said preferred amount indicated by target values for absorption and scattering coefficients, said coefficients being calculated for successive spectral measurements.

37. The apparatus of claim 25, wherein said system for raising and lowering said platform comprises one of:
   a hand crank;
   a lever arm;
   a scissors jack
   a hinge point in conjunction with a linear drive; and
   a worm drive.

38. The apparatus of claim 1, wherein said means for reproducibly positioning said tissue measurement site relative to said subject interface comprises a placement guide, said placement guide being reproducibly attachable to a subject's body part whereon said tissue measurement site is located, said guide having an aperture through which said subject interface protrudes to contact said tissue measurement site, said placement guide also having one or more guide rods for reproducibly coupling an analyzer bearing said subject interface to said tissue measurement site.

39. The apparatus of claim 38, wherein said body part comprises a limb of said subject.

40. A method for varying localized absorption and scattering coefficients at a tissue measurement site in a controlled and reproducible manner during optical sampling of a tissue volume comprising the steps of:
   providing a tissue measurement site;
   providing a spectroscopic analyzer having a subject interface adapted to make contact with said tissue measurement site during measurement;
   making an initial NIR spectral measurement, for which any of applied pressure to the tissue measurement site by said subject interface and degree of displacement into the tissue of the tissue measurement site by said subject interface is known and maintained during said initial measurement;
   measuring NIR spectral data of tissue at said tissue measurement site;
   varying and maintaining contact with said tissue measurement site by said subject interface in a controlled and reproducible manner according to said measured NIR spectral data;
   calculating local absorbance and scattering coefficients for said measurements;
   making one or more subsequent NIR spectral measurements in which any of applied pressure and displacement is varied by a known amount;
   calculating absorbance and scattering coefficients for each measurement; and
   determining an optimal sampling depth for detecting a target analyte, wherein a ratio of absorption coefficient to scattering coefficient is an indicator of said optimal depth.

41. The method of claim 40, wherein increased pressure at said tissue measurement site forces water from said sampled tissue volume, and wherein the local absorption coefficient decreases as water concentration within said tissue volume decreases.

42. The method of claim 41, wherein density of scattering centers within said sampled tissue increases as water concentration decreases, and wherein said scattering coefficient increases as density of scattering centers increases.

43. The method of claim 42, wherein said tissue measurement site is on a limb of a living subject.

44. The method of claim 43, wherein said limb is an arm.

45. The method of claim 42, wherein said subject interface comprises a fiber optic probe having a tip, and wherein said probe delivers light energy to said tissue measurement site and collects light energy transmitted or reflected from said tissue measurement site.

46. The method of claim 45, wherein said tip contacts said tissue measurement site.

47. The method of claim 42, wherein a guide positions said tissue measurement sight relative to said subject interface in a controlled and reproducible manner.

48. The method of claim 47, wherein said guide includes an aperture, wherein said subject interface protrudes through said aperture to contact said tissue measurement site.

49. The method of claim 42, wherein said applied pressure is varied and controlled by means of a single arm balance having an adjustable counter weight, said balance comprising a beam having a first end and a second end, wherein said pressure is controlled and varied by adjusting said counterweight.

50. The method of claim 49, wherein said balance further comprises a gimbal mount attached to an end of said balance, wherein said subject interface floats on said gimbal mount.

51. The method of claim 50, wherein said balance further comprises a locking mechanism so that said beam may be locked into a desired position.

52. The method of claim 42, wherein said degree of displacement is varied and controlled by a platform having one or more guides for reproducibly positioning said tissue measurement site, said platform being supported on and attached to a system for raising and lowering said platform so that said subject interface may contact said tissue measurement site and then be displaced into skin at the tissue measurement site by a known amount, where said subject interface is fixedly mounted.

53. The method of claim 52, wherein a zero point constitutes the first point of full contact between said subject interface and said tissue measurement site, wherein said tissue measurement site is first lowered to said zero point and subsequently lowered a further known amount to displace said subject interface further into the tissue measurement site.

54. The method of claim 52, wherein said means for raising and lowering said platform comprises a linear actuator, said linear actuator powered by an electric motor.

55. The method of claim 54, wherein said electric motor is digitally-controlled.

56. The method of claim 52, wherein said means for raising and lowering said platform comprises one of:

a hand crank;

a lever arm;

a scissors jack a hinge point in conjunction with a linear drive; and a worm drive.

* * * * *